United States Patent [19]

Kaneko et al.

[11] 4,450,001

[45] May 22, 1984

[54] ANIONIC BIOCIDE EMULSIONS IN AQUEOUS SOLUTIONS OF STRONGLY IONIZABLE SALTS

[75] Inventors: Thomas M. Kaneko, Trenton; Daniel R. Dutton; Bongsub Kim, both of Grosse Ile, all of Mich.

[73] Assignee: BASF Wyandotte Corporation, Wyandotte, Mich.

[21] Appl. No.: 122,209

[22] Filed: Feb. 19, 1980

[51] Int. Cl.³ .................... A01N 37/18; A01N 33/02
[52] U.S. Cl. .................................. 71/118; 71/121; 71/DIG. 1; 71/65; 71/79; 71/28; 71/59; 71/3; 252/174.16; 252/352; 252/354; 252/356; 252/DIG. 17
[58] Field of Search .................. 71/DIG. 1, 118, 65, 71/79, 3

[56] References Cited

U.S. PATENT DOCUMENTS

| | | | |
|---|---|---|---|
| 3,172,750 | 3/1965 | Altscher et al. | 71/DIG. 1 |
| 3,236,627 | 2/1966 | Lindner | 71/3 |
| 3,713,804 | 1/1973 | Moccia | 71/DIG. 1 |
| 3,834,935 | 9/1974 | Symm et al. | 117/138.8 B |
| 3,986,862 | 10/1976 | Armstrong | 71/118 |
| 4,182,621 | 1/1980 | Ogata et al. | 71/DIG. 1 |

OTHER PUBLICATIONS

Kuwamura et al, "Surface Active Block, etc.;" (1970) J. Am. Oil Chem. Soc. 48 pp. 29–34 (1971).
McCutcheon I, "D & E Int. Ed. 1976 Ann." (1976) MC Pub. Co. Ridgewood, N.J. pp. 9, 59 (1976).
McCutcheon II, "D & E 1971 Ann." (1971) Allured Pub. Co. Ridgewood, N.J. pp. 219–222 (1971).

*Primary Examiner*—Glennon H. Hollrah
*Attorney, Agent, or Firm*—Bernhard R. Swick

[57] ABSTRACT

Highly stable emulsions of biocides in liquid fertilizer compositions are disclosed which offer unexpected stability thus permitting application of both biocides and liquid fertilizers simultaneously. The improved emulsion stability can be obtained by utilizing higher polyoxyalkylene glycol ethoxylate esters or combinations thereof with certain anionic emulsifiers. Stable aqueous emulsions are also disclosed.

14 Claims, No Drawings

ANIONIC BIOCIDE EMULSIONS IN AQUEOUS SOLUTIONS OF STRONGLY IONIZABLE SALTS

BACKGROUND OF THE INVENTION

1. Field of the Invention

This invention relates to surfactant compositions which are effective in dispersing water-insoluble liquids in aqueous liquids or aqueous solutions of strongly ionizable salts.

2. Description of the Prior Art

The use of biocides, which term includes various toxicants separately classified as insecticides, fungicides, weed killers, insect repellants, nematocides, rodenticides, etc., is widespread in the agricultural industry where it is conventional to apply the biocide as an aqueous dispersion or emulsion. The application of combinations of biocides and liquid fertilizers in a single stage results in savings of labor and provides efficient use of spray application equipment.

The use of liquid fertilizer compositions with various herbicides is discussed by Lindner in Chapter 4 of *Pesticide Formulations*, edited by W. Van Valkenburg, Marcel Dekker, Inc., New York, 1973. Lindner in U.S. Pat. No. 3,236,627 provides dispersants useful in preparing liquid fertilizer biocide emulsions which exhibit stability only over periods of several hours. The blend of surfactants disclosed by Lindner can be, for instance, a mixture of the adduct of one mole of nonylphenol and one mole of ethylene oxide with maleic anhydride to form the monomaleic acid ester of nonylphenol mono-ethylene glycol monoether which is further reacted with ammonium bisulfite to produce the sulfosuccinic acid ester thereof. The alkali metal or ammonium salt thereof is useful in combination with a second surfactant component which is an mono-ethylene glycol monoether which is further reacted with ammonium bisulfite to produce the sulfosuccinic acid ester thereof. The alkali metal or ammonium salt thereof is useful in combination with a second surfactant component which is an amine salt of an alkyl benzene sulfonic acid. In U.S. Pat. No. 3,317,305, there is provided a phosphate ester emulsifier as a means of providing stable emulsions of various biocides in liquid fertilizer compositions containing high concentrations of electrolytes and/or other nutrient materials such as urea.

In no one of the above prior art references is there disclosed the use of a single anionic stabilizer or combination thereof with a conventional anionic emulsifier to provide stable emulsions of various biocides in commonly-used liquid fertilizer solutions containing strongly ionizable salts, as well as other nutrients such as urea.

SUMMARY OF THE INVENTION

There are disclosed surfactant compositions useful in providing stable emulsions of at least one biocide in aqueous liquids or aqueous liquid fertilizer compositions containing strongly ionizable salts. It has been found that certain polyoxyalkylene glycol esters are useful alone or in combination with conventional anionic surfactants in providing stability under adverse aqueous emulsion conditions wherein strongly ionizable salts are present such as in liquid fertilizer compositions. The anionic emulsifiers useful in the invention are polybasic acid esters of ethoxylated polyoxyalkylene glycols wherein the alkylene group has 4 carbon atoms and can be selected from the group consisting of oxybutylene, the residue of tetrahydrofuran, and mixtures thereof. Such anionic surfactants can be used alone or in combination with at least one of certain conventional anionic surfactants, namely, water-soluble salts of alkylaromatic sulphates, phosphates, sulfonates, and phosphonates. Said alkylaromatic esters are preferably utilized in the form of their ammonium, alkali metal, and alkaline earth metal salts.

DESCRIPTION OF THE PREFERRED EMBODIMENTS

It has been discovered that certain anionic surfactants unexpectedly provide stable combinations of at least one biocide in aqueous liquids and aqueous liquid fertilizer compositions. The stable emulsions of the invention overcome the instability of prior art emulsion systems of biocides and liquid fertiizer solutions, thus overcoming the filter screen clogging of agricultural spray equipment. These anionic surfactants are derived from the reaction of an alkylene oxide having 4 carbon atoms with an initiator compound having at least 2 active hydrogens. The oxyalkylene polyols so prepared are further reacted with ethylene oxide and then esterified to produce the anionic polyoxyalkylene glycol ester surfactant utilized in the invention.

The anionic glycol-ester surfactants useful in providing stable emulsions of biocides in liquid fertilizer compositions are polybasic acid esters of the hydroxyl-terminated oxyalkylene polyols represented by the formula

wherein Y is the residue formed by the removal of x atoms of active hydrogen from an initiator containing at least 2 active hydrogens capable of reacting with an alkylene oxide, A is the residue of an alkylene oxide having 4 carbon atoms selected from the group consisting of oxybutylene, the residue of tetrahydrofuran, and mixtures therof, x is an integer of at least 2, preferably 2 to 5, n is an integer such that the total oxyalkylene content excluding ethylene oxide, nx is sufficient to provide a molecular weight of about 1000 to about 2500, preferably about 1200 to about 1800, and m is an integer such that the oxyethylene content of the polymer, mx is sufficient to provide about 20 to about 80 percent, preferably about 30 to about 70 percent, by weight of the total molecular weight of the polymer.

The initiator can be substantially any compound capable of reacting with an alkylene oxide having at least 2, preferably 2 to 6 active hydrogen atoms, and most preferably 2 to 3 active hydrogen atoms. Many known compounds fulfill this requirement. Preferably, the initiator contains up to 20 carbon atoms and is free of elements other than carbon, hydrogen, oxygen, and nitrogen. Representative initiators are selected from at least one of the following classes of compounds having at least 2 active hydrogen atoms: aliphatic (including both open chain and cyclic compounds) and aromatic (including both mononuclear and polynuclear compounds) carboxylic acids; alkylene diols, triols, and polyols; alkanols; phenols; amines and alkanolamines. The preferred initiators are alkylene diols having a carbon chain length of 2 to 6. Examples of useful initiators within these classes are: the aliphatic dicarboxylic acids such as oxalic, malonic, succinic, glutaric, adipic, pimelic, suberic, azelaic, sebacic, maleic, fumaric; the aromatic dicarboxylic acids such as phthalic, isophthalic, terephthalic; the alkylene glycols such as ethylene glycol, and propylene glycol alkanols such as 1,4-butanediol; the polyalkylene glycols such as polyethylene glycol, polybutylene glycol, and polypropylene glycol; polyols such as glycerol, polyglycerol, trimethylolpropane, sorbitol, glucose, and sucrose, pentaerythritol, and aerythritol; phenols such as hydroquinone, resorcinol, and bisphenol A; alkanolamines such as ethanolamine, diethanolamine, and triethanolamine; and amines such as the aromatic amines, aniline and phenylene polyamine, and the aliphatic amines such as ethylene diamine and diethylene triamine.

Any polybasic acid can be used in the preparation of the polyoxyalkylene esters employed in accordance with the present invention. Illustrative acids include inorganic acids such as phosphoric acid, phosphorus acid, and boric acid; aliphatic organic acids such as malonic acid, succinic acid, glutaric acid, adipic acid, maleic acid, fumaric acid, malic acid, oxalic acid, tartaric acid, and diglycolic acid; and aromatic organic acids such a phthalic acid, terephthalic acid, isophthalic acid, trimellitic acid, and mixtures thereof. It will be understood that the anhydrides of any of the above acids where they exist can be used alternatively to the use of the acids in the preparation of the esters of the invention.

In the preparation of the polyoxyalkylene esters, which are employed in accordance with the present invention, it is preferred to employ at least equal molar amounts of acids or their anhydrides or an excess of that required for complete esterification of the polyols. Thus, for example, one mole of a polyol is prepared by reacting 1,2-butylene oxide utilizing 1,4-butanediol as an initiator to obtain a molecular weight of about 1200 in the condensation product. Said product is further reacted with sufficient ethylene oxide to provide approximately 40 percent by weight, based upon the total weight of the polyol and then esterified with at least one mole, but preferably 2 moles, of a dibasic acid such as maleic acid. One skilled in the art will understand that the esterification product is often a mixture of completely esterified polyol and partially esterified polyol. Where an equivalent amount of polybasic acid is used, the esterification product will contain a predominance of the half-ester.

At least one of the above-described glycol-ester anionic surfactant can be utilized as the sole emulsifying agent to provide stable mixtures of various biocides and liquid fertilizer compositions. Increased stability can be obtained, by admixing said glycol-ester anionic surfactant with at least one additional conventional emulsifying agents, particularly certain conventional anionic alkylaromatic sulphur- or phosphorus-containing ester emulsifying agents. Said conventional anionic surfactants are more particularly the anionic alkylaromatic sulfate, phosphate, sulfonate and phosphonate esters which are used in the form at least one of their water-soluble salts such as the ammonium, alkaline earth metal, and alkali metal salts thereof. Useful alkali metal salts are: lithium, sodium, potassium, rubidium, and a caesium. Useful alkaline earth metal salts are: beryllium, magnesium, calcium, strontium, zinc, cadmium, and barium. The useful alkylaromatic sulfur- or phosphorus-containing ester salts generally have an HLB of at least 15. Salts having HLB values of up to 45 are useful. The water-soluble salts of alkylaromatic sulfate, phosphate, sulfonate and phosphonate esters are well known in the art. These generally have about 9 to about 18, preferably about 12 to about 18, carbon atoms in the alkyl substituent. Representative anionic surfactants are calcium and magnesium dodecyl benzene sulphonate and calcium and magnesium nonylphenol sulphonate.

The proportion of surfactant or emulsifier utilized in the formation of emulsions of the biocide in the liquid fertilizer composition is generally about 1 to about 10 percent by weight of the surfactant and about 99 to about 90 percent by weight of biocide based upon the total weight of the biocide and emulsifier. Such mixtures of biocide and surfactant constitute an emulsifiable concentrate. Preferably, about 2 to about 8 percent by weight of the emulsifier is utilized and most preferably, about 4 to about 6 percent by weight of emulsifier is utilized. Where mixtures of anionic surfactants are utilized as emulsifier, the proportions of said glycol-ester anionic to conventional anionic surfactant are generally about 50 to about 95 percent by weight of said glycol-ester anionic surfactant and about 5 to about 50 percent by weight of said conventional anionic surfactant, preferably about 60 to about 90 percent by weight of the glycol-ester anionic surfactant and about 10 to abbut 40 percent by weight of the conventional anionic surfactant, based upon the total weight of emulsifier utilized. It will be understood that mixtures of at least one of the anionic glycol-ester surfactants disclosed with at least one of the conventional anionic surfactants disclosed can be employed in the practice of the present invention. In addition, it will be recognized that the surfactant ingredients can be utilized in the form of impure reaction products containing high percentages of the active constituents thereof. Generally, about 1 to about 5 percent by weight emulsifiable concentrate is utilized to 99 to 95 percent by weight of fertilizer, all based upon total weight of said biocide-liquid fertilizer emulsions. Preferably, 2 to about 4 percent of said concentrate is used.

The biocides, which are useful, are selected from any of the known biocides, particularly herbicides and insecticides, which are useful in combination with liquid fertilizers, as listed on page 132 by Lindner in *Pesticide Formulations,* edited by W. Van Valkenburg, incorporated herein by reference. Particularly useful are herbicides such as 2-chloro-2'-6'-diethyl-N(methoxymethyl)-acetanilide; a,a,a-trifluoro-2,6-dinitro-N,N-dipropyl-p-toluidene; and N-(1-ethylpropyl)-3,4-dimethyl-2,6-dinitrobenzenamine. Other useful biocides are listed in U.S. Pat. No. 3,317,305, incorporated herein by reference.

In order to emulsify any of the above biocides, it is necessary that the biocide be in the form of a liquid. Generally, the biocides are solids or liquids and where solids these must be combined with a liquid solvent in a minor amount, generally just enough to render the solid biocide liquid in form. Thus, where any of the above biocides are sold as solids, it is necessary, in order to emulsify these biocides, that they be combined with a suitable organic solvent in order to effect the emulsification in a liquid fertilizer composition. Generally, the organic solvents utilized to render liquid the solid biocides are chosen from aromatic, aliphatic, cycloaliphatic, or heterocyclic organic solvents which are insoluble in the aqueous phase of the liquid fertilizer. The type of organic solvent is not critical. Generally, it is preferable to utilize an aromatic solvent carrier because of the ready availability and low cost thereof. Examples of suitable aromatic solvents are benzene, toluene, xylene, as well as commercial products which are primarily hydrocarbon in nature and which contain a high aromatic content. Thus, suitable solvents are the commercially-available kerosene, mineral spirits, mineral oil, methylnaphthalenes, i.e., monomethyl naphthalene, dimethyl naphthalene, and trimethylnaphthalene, ethyl naphthalene, cyclohexane, 2-methylpentane diol-1,2, dipropylene glycol methyl esters, tetrahydronaphthalene, and other similar products. In certain instances, the liquid carrier solvent will be a chlorinated hydrocarbon, said solvents being selected over the lower cost aromatic hydrocarbons because the particular biocide is not soluble or sufficiently soluble in the aliphatic or aromatic hydrocarbons generally used. Representative chlorinated hydrocarbons are monochlorobenzene, perchloroethylene, and carbon tetrachloride. Generally about 30 percent to about 60 percent, preferably about 40 percent to about 55 percent by weight of said solvent is used, all based upon the total weight of said biocide and said liquid solvent.

Generally, it is desirable to combine the surfactant compositions of the invention with the liquid biocide compositions so that an emulsifiable concentrate is formed which can be directly mixed into a liquid fertilizer composition and emulsified without special mixing procedures. Because both types of anionic surfactants useful in emulsifying the biocide in the liquid fertilizer composition of this invention are foaming agents as well as emulsifying agents, it is often desirable to include in the surfactant portion of the emulsifiable concentrate a conventional defoaming agent, particularly a nonionic defoaming agent. The emulsification of the biocide in the liquid fertilizer composition can proceed with only an oxyalkylene glycol-ester anionic surfactant, as described, or alternatively a mixture of said glycol-ester and conventional anionic surfactant, as described. A conventional defoaming agent can be utilized in combination with the emulsifying surfactants as an optional ingredient where foam control is desirable.

Suitable conventional nonionic defoaming agents are well known in the art and include, for instance, conjugated polyoxyalkylene compounds such as certain compounds described in U.S. Pat. No. 2,677,700, incorporated herein by reference, or certain of the compositions more particularly described in U.S. Pat. Nos. 2,674,619 and 2,979,528, both incorporated herein by reference. Of particular usefulness are the polyoxyalkylene surfactants having a cloud point in a 1 percent aqueous solution of about 10° C. to about 30° C., preferably about 10° C. to about 25° C., and most preferably about 15° C. to about 25° C., which have the formulas:

$$Y[(EO/A)_m(A)_nH]_x \qquad \text{I}$$

$$Y[(A)_o(EO)_m(A)_nH]_x \qquad \text{II}$$

$$Y[(A)_o(EO/A)_m(A)_nH]_x \qquad \text{III}$$

$$Y[(EO/A)_m(EO/A)_n)H]_x \qquad \text{IV}$$

wherein EO represents ethylene oxide which is present in the polymer in the proportion of about 5 to about 60 percent, preferably about 5 to about 25 percent, and most preferably about 5 to about 15 percent all by weight; Y represents the nucleus of an active hydrogen-containing organic compound having a functionality x and (1) about 2 to about 6 carbon atoms and at least two reactive hydrogen atoms or (2) about 7 to about 18 carbon atoms and at least one reactive hydrogen atom; A represents an alkylene oxide selected from the group consisting of propylene oxide, butylene oxide, tetrahydrofuran, or mixtures thereof; EO/A represents a mixture of ethylene oxide and a lower alkylene oxide in which EO and A are present in the proportions by weight of 5 to 95 to 95 to 5 percent; wherein up to 25 percent by weight of A is reacted directly with said organic compound either alone (in formulas II and III) or in admixture with ethylene oxide (in formulas I and IV) and 75 percent by weight or more of A is subsequently reacted to produce said polymer; m, n and o are integers individually selected such that said polymer has an average total molecular weight generally of about 500 to about 25,000.

Other polyoxyalkylene surfactants having a cloud point in a 1 weight percent aqueous solution of about 10° C. to about 20° C. and preferably about 15° C. to about 20° C., are also useful in blends with conventional low-foaming nonionic surfactants. These have the formula:

$$Y[(EO)_m(A)_nH]_x \qquad \text{V}$$

where Y, EO, A, m, n, x, molecular weight and useful proportions are as defined herein for formulas I–IV.

The above-described nonionic defoamers are utilized in the emulsifiable concentrates as a portion of the surfactant component of said emulsifiable concentrates. The defoamers are present in relatively small amounts, generally about 10 to about 25 percent by weight of the surfactant component of the emulsifiable concentrate is at least one of the above-described nonionic defoaming agents.

The liquid fertilizer solutions useful in forming the stable biocide-liquid fertilizer compositions of the invention comprise aqueous solutions of strongly ionized water-soluble compounds which provide a source of nitrogen either alone or in combination with urea. Generally, these liquid fertilizer solutions contain about 20 to about 50 percent by weight solids, preferably about 25 to about 40 percent solids. The useful liquid fertilizer types, namely mixtures of aqueous ammonia, ammonium nitrate, urea, and water (Uran types), nitrogen solutions containing ammonia, ammonium nitrate, and water, with or without urea (Nitrana and Urana types), and ammonium nitrate solutions (Feran type) are examples of liquid fertilizer mixtures susceptible to combination with various biocides by the use of the disclosed nonionic surfactant or blend of nonionic and anionic surfactants disclosed herein. It is recognized that, in addition to the electrolytes in the liquid fertilizer compositions above, other sources of nutrient materials are often present in the aqueous solution. Among such additonal nutrients, urea is often utilized since it is a valuable source of nitrogen but, of course, is not an electrolyte. The useful aqueous fertilizer compositions are either neutral or substantially neutral, for example, a mixture of urea and ammonium nitrate is neutral. Stable aqueous emulsions in aqueous liquids having hardness levels of about 100, 300, and 1000 can also be obtained using the emulsifiers of the invention.

In order to evaluate the stability of emulsions formed utilizing various liquid biocides in combination with the surfactant blends of the invention, the biocide under test is prepared utilizing a standard amount of emulsifier. In the test described herein, the amount of emulsifier is 5 percent by weight based upon the total weight of the liquid biocide and the emulsifier. The combination of a biocide and the disclosed surfactant of the invention results in an emulsifiable concentrate of the biocide. For the purposes of evaluation herein, a liquid 28 percent by weight nitrogen fertilizer solution was prepared by dissolving 496.4 grams of ammonium nitrate and 396.8 grams of urea in 386.56 grams of distilled water. Prior to use, the composition is stored above 0° C.

The following apparatus is required to perform the test used herein to evaluate the stability of emulsions of a biocide in a 28 percent by weight nitrogen solution fertilizer. Babcock milk test bottles and measuring pipettes having a long tip, for instance, 2 milliliter capacity pipettes, and No. 0 (zero) cork stoppers. A method of measuring short durations of time complete the list of equipment needed. The test procedure is initiated by determining the stem volume of each particular Babcock bottle which is to be utilized. This value is subsequently used in determining the amount of the biocide-liquid fertilizer emulsion required to perform the test. To start the test, 40 milliliters of the liquid fertilizer are poured into the test bottle using a conical funnel attached to a disposable pipette. This is followed by a volume of the biocide concentrate under test, which is added by pipetting said biocide into the test bottle, in an amount exactly equal to the stem volume of the test bottle (approximately 1.6 milliliters). The test bottle is then stoppered and vigorously shaken by hand using an up and down motion for 60 cycles over a period of one minute. Should excessive foaming develop during shaking, one-half drop of an antifoam agent can be added to the bottom portion of the stopper on a successive test prior to beginning shaking. The stopper is removed after shaking and the contents of the bottle are carefully diluted to the level of the top of the meniscus appearing on the top graduation of the bottle stem. The stopper is then replaced and the bottle is inverted 15 times before being returned to upright position. After a period of 15 minutes, the volume percent separation is read directly on the graduations of the bottle. Since the total volume of the biocide added is equal to the volume of the stem which is divided into 80 equal parts, each portion represents $1/80 \times 100$ percent or 1.25 percent of the formulation added.

The following examples illustrate the various aspects of the invention but are not intended to limit its scope. Where not otherwise specified throughout this specification and claims, temperatures are given in degrees centigrade and parts, percentages and proportions are by weight.

EXAMPLE 1

An emulsifiable concentrate is prepared utilizing 95 parts by weight of a liquid biocide which is a mixture of 44 percent by weight active 2-chloro-2'-6'-diethyl-N-(methoxy-methyl)-acetanilide in xylene, 4 parts by weight of the maleic acid half-ester of ethoxylated polybutylene glycol initiated with 1,4-butanediol having a molecular weight of about 1200 in the hydrophobic butylene glycol portion thereof in which the ethylene oxide content is 60 percent by weight of the total molecular weight of the polymer, and 1 part by weight of a low-foaming nonionic surfactant sold under the tradename TETRONIC®150R-1. The low-foaming nonionic is a block polyol having a molecular weight of about 8000 prepared by successively condensing propylene oxide and ethylene oxide in a weight ratio of propylene oxide to ethylene oxide of 9:1 with the tetrafunctional initiator N,N,N',N'-tetrakis(2-hydroxypropyl)ethylene diamine. The maleic acid ester was made by reacting in a 1:1 molar ratio, maleic anhydride and said ethoxylated polybutylene glycol under esterification conditions.

The emulsifiable concentrate and the biocide are mixed together in a suitable mixing device to prepare the emulsifiable concentrate. This concentrate is then utilized in the test method described above for determining the emulsion stability of a biocide emulsifiable concentrate in the 28 percent by weight ammonium nitrate-urea-water liquid fertilizer composition described above. The composition prepared passes the above test procedure by showing no separation after a period of 15 minutes.

EXAMPLE 2

Example 1 is repeated substituting the maleic acid half-ester of a 1,4-butanediol initiated-polybutylene glycol ethoxylate having a molecular weight in the butylene oxide-derived hydrophobe of about 1200 and having 40 percent by weight of the polymer derived from ethylene oxide. Similar results are obtained upon combining the emulsifiable concentrate made therewith and the liquid fertilizer solution.

EXAMPLE 3

An emulsifiable concentrate is prepared utilizing 95 percent by weight of the liquid biocide of Example 1, previously identified as to chemical composition, together with 5 percent by weight of a mixture of the following ingredients in percent by weight:
- the maleic acid half-ester of a 1,4-butanediol initiated-polybutylene glycol, about 1200 molecular weight in the butylene oxide hydrophobe and 40 percent of the total molecular weight of the polymer derived from ethylene oxide—3 percent,
- a nonionic defoamer sold under the tradename TETRONIC®150-R-1, previously described herein,—1.16 percent,
- calcium dodecylbenzene sulfonate—0.45 percent, and 2-ethylhexanol—0.39 percent.

The emulsifiable concentrate is prepared by admixing the ingredients and stirring utilizing suitable mixing apparatus. When the emulsifiable concentrate is mixed with the liquid fertilizer solution of Example 1 in the same proportions as described herein, a stable emulsion is formed.

EXAMPLE 4

Utilizing the procedure and proportions of Example 3, a maleic acid half-ester of a 1,4-butanediol initiated-polybutylene glycol ethoxylate having a molecular weight of about 1200 in the hydrophobic portion thereof and in which ethylene oxide accounts for about 60 percent by weight of the molecular weight of the polymer, is evaluated by substituting this surfactant for the polybutylene glycol ester surfactant of Example 3. Similar results are obtained when the emulsifiable concentrate made herein is admixed with the liquid fertilizer composition in accordance with the above-described test procedure.

EXAMPLES 5-7

Examples 3 and 4 are repeated utilizing as the biocide a mixture of 50 percent by weight active a,a,a-trifluoro-2,6-dinitro-N,N-dipropyl-p-toluidine in xylene substituted for the biocide of Example 1. Similar results are obtained.

Example 3 is repeated utilizing as the biocide a mixture of 42.5 percent by weight active N-(1-ethylpropyl)-3,4-dimethyl-2,6-dinitrobenzeneamine in xylene substituted for the biocide of Example 3. Similar results are obtained.

EXAMPLE 8

(control—forming no part of this invention)

Example 1 was repeated using 5 parts by weight of calcium dodecylbenzene sulfonate and 95 parts by weight of the herbicide of Example 1 to prepare an emulsifiable concentrate. When this was admixed with the liquid test fertilizer solution utilized in the above examples, greater than 100 percent separation occured, indicating failure in the test for emulsion stability.

EXAMPLES 9–13

Examples 3–7 are repeated utilizing a liquid fertilizer aqueous solution containing 30 percent by weight ammonium nitrate instead of the 28 percent by weight solids ammonium nitrate, urea, and water-containing liquid fertilizer test solution. A stable emulsion is obtained in each example.

EXAMPLES 14–20

Examples 1–7 are repeated using water to replace the liquid fertilizer test solution. Water having hardness levels expressed in ppm of calcium carbonate of about 100, 300 and 1000 ppm is used. Stable emulsions are obtained.

While this invention has been described with reference to certain specific embodiments, it will be recognized by those skilled in the art that many variations are possible without departing from the scope and spirit of the invention and it will be understood that it is intended to cover all changes and modifications of the invention disclosed herein for the purposes of illustration which do not constitute departures from the spirit and scope of the invention.

The embodiments of the invention in which an exclusive privilege or property is claimed are defined as follows:

1. An emulsifiable concentrate adapted for use in forming aqueous emulsions suitable for spray application comprising about 90 to 99 percent by weight of at least one liquid biocide and about 1 to about 10 percent by weight of at least one polyoxyalkylene ester surfactant said ester being the reaction product of a polybasic acid or anhydride with a polyoxyalkylene glycol ethoxylate having the formula $$Y[(A)_{\overline{n}}(C_2H_4O)_{\overline{m}}H]_x$$

wherein A is an alkylene oxide having 4 carbon atoms and selected from the group consisting of oxybutylene, the residue of tetrahydrofuran, and mixtures thereof; Y is an initiator having up to 20 carbon atoms and free of elements other than carbon, hydrogen, oxygen and nitrogen and x is an integer of at least 2, n is an integer such that the molecular weight is about 1000 to about 2500, m is an integer such that the oxyethylene content of the entire compound, mx oxyethylene groups, constitutes about 20 to about 80 percent by weight of the total oxyalkylene content or
the surfactant blend comprising said polyoxyalkylene ester surfactant and at least one other anionic, alkyl aromatic sulfur- or phosphorus-containing ester surfactant having an HLB of at least 15 and about 9 to about 18 carbon atoms in the alkyl group.

2. The composition of claim 1 wherein said biocide comprises a herbicide selected from at least one of the group consisting of 2-chloro-2'-6'-diethyl-N-(methoxymethyl)acetanilide; a,a,a-trifluoro-2,6-dinitro-N,N-dipropyl-p-toluidine; and N(1-ethylpropyl)-3,4-dimethyl-2,6-dinitrobenzenamine and said initiator is a compound selected from at least one member of the group consisting of the following classes of compounds having 2 to 6 active hydrogen atoms: carboxylic acids; alkylene diols, triols, and polyols; alkanols; phenols; amines; and alkanolamines.

3. The composition of claim 2 wherein said surfactant blend is a mixture of about 50 to about 95 percent by weight of said polyoxyalkylene ester surfactant wherein said ester is the half-ester of polybasic acids selected from the group consisting of phosphoric acid, phosphorus acid, boric acid, malonic acid, succinic acid, glutaric acid, adipic acid, maleic acid, fumaric acid, malic acid, oxalic acid, tartaric acid, diglycolic acid, phthalic acid, terephthalic acid, isophthalic acid, trimellitic acid, and mixtures thereof and about 5 to about 50 percent by weight of said other anionic surfactant and wherein said polyoxyalkylene ester surfactant is an alkylene glycol-initiated reaction product of 1,2-butylene oxide and ethylene oxide wherein the residue of butylene oxide is present in an amount sufficient to provide a molecular weight of about 1000 to about 2500 and wherein the oxyethylene content is about 30 to about 70 percent by weight of the total molecular weight of said polyoxyalkylene ester surfactant and wherein the other anionic surfactant is selected from at least one of the group consisting of the water-soluble salts of alkylaromatic sulfonates, phosphonates, sulphates, and phosphates having about 9 to about 18 carbon atoms in the alkyl group.

4. The composition of claim 3 wherein said polyoxyalkylene ester surfactant is the maleic acid half-ester of a 1,4-butanediol-initiated ethoxylate reaction product having a molecular weight of about 1200 in the butylene oxide derived hydrophobe, 60 percent by weight of the total molecular weight of said ethoxylate is derived from ethylene oxide, and said other anionic surfactant is selected from at least one of the group consisting of the ammonium, alkaline earth, and alkali metal salts of dodecylbenzene sulfonate, and wherein said polyoxyalkylene ester surfactant is present in the amount of 60 percent by weight and said anionic surfactant is present in the amount of 9 percent by weight, all based on the total weight of said surfactant blend, and wherein said surfactant blend constitutes 5 percent by weight of the total weight of said emulsifiable concentrate.

5. The composition of claim 4 wherein said anionic surfactant is calcium dodecylbenzene sulfonate.

6. The emulsifiable concentrate of claim 3 wherein said polyoxyalkylene ester surfactant is a 1,4-butanediolinitiated ethoxylate reaction product having a total molecular weight of about 1200 in the butylene oxide derived hydrophobe and wherein the oxyethylene content is 40 percent by weight of the total weight of said ethoxylate, said other anionic surfactant is present in the amount of 9 percent by weight, selected from the group consisting of the ammonium, alkaline earth, and alkali metal salts of dodecylbenzene sulfonate and said nonionic surfactant is present in the amount of 60 percent by weight, all based upon the total weight of said surfactant blend which constitutes 5 percent by weight of the total weight of said emulsifiable concentrate.

7. The composition of claim 6 wherein said anionic surfactant is calcium dodecylbenzene sulphonate.

8. An aqueous dispersion of an emulsifiable liquid biocide concentrate comprising at least one emulsifying agent and at least one biocide, said emulsifying agent being present in sufficient amount to provide a stable aqueous dispersion in an aqueous liquid of said biocide, wherein said dispersion contains sufficient emulsifiable concentrate to provide a solids content of said concentrate of about 1 to about 5 percent by weight based upon the total weight of the said dispersion and wherein said emulsifying agents and said biocide constitute, in admixture, an emulsifiable concentrate having the composition of claim 1.

9. The aqueous dispersion of claim 8 wherein said aqueous liquid is water, said liquid biocide is a herbicide selected from at least one of the group consisting of 2-chloro-2′-6′-diethyl-N-(methoxy methyl)-acetanilide, a,a,a-trifluoro-2,6-dinitro-N,N-dipropyl-p-toluidine, and N(1-ethylpropyl)-3,4-dimethyl-2,6-dinitrobenzenamine and wherein said emulsifying agent is the surfactant blend of claim 1 and said initiator is a compound selected from at least one member of the group consisting of the following classes of compounds having 2 to 6 active hydrogen atoms: carboxylic acids; alkylene diols, triols, and polyols; alkanols; phenols; amines; and alkanolamines.

10. The aqueous dispersion of claim 9 wherein said surfactant blend contains about 50 to about 95 percent by weight of said polyoxyalkylene ester surfactant and about 5 percent to about 40 percent of said anionic surfactant and wherein said polyoxyalkylene ester surfactant is the polybasic acid ester of acids selected from the group consisting of phosphoric acid, phosphorus acid, boric acid, malonic acid, succinic acid, glutaric acid, adipic acid, maleic acid, fumaric acid, malic acid, oxalic acid, tartaric acid, diglycolic acid, phthalic acid, terephthalic acid, isophthalic acid, trimellitic aid, and mixtures thereof and a 1,4-butane diol-initiated 1,2-butylene oxide-ethylene oxide reaction product having a molecular weight of about 1000 to about 2500 in the hydrophobic butylene oxide-derived portion of the polymer and wherein the oxyethylene content of the polymer is sufficient to provide about 30 to about 70 percent by weight of the total molecular weight of the polymer and wherein said other anionic surfactant is selected from at least one of the group consisting of at least one of the water-soluble salts of alkylaromatic phosphates, sulphates, sulfonates, and phosphonates.

11. The aqueous dispersion of claim 10 wherein the proportion of said biocide is about 90 to 99 percent by weight and wherein the proportion of said emulsifying agent in said surfactant blend is about 1 to about 10 percent by weight of the total weight of the mixture of said biocide and said emulsifying agents and said other anionic surfactant is selected from at least one of the group consisting of the ammonium, alkaline earth, and alkali metal salts of an alkylaromatic sulfonate.

12. The aqueous dispersion of claim 11 wherein said surfactant blend is a mixture of a polyoxyalkylene ester and an other anionic surfactant wherein said ester is a maleic acid half-ester of a 1,4-butanediol-initiated reaction product of 1,2-butylene oxide and ethylene oxide in sufficient amount to provide a molecular weight of about 1200 for the hydrophobic butylene oxide-derived portion of said product, the oxyethylene content being sufficient to provide about 30 to about 70 percent by weight of the total molecular weight of the polymer and said other anionic surfactant is the calcium salt of an alkylaromatic sulfonate having about 9 to about 18 carbon atoms in the alkyl group.

13. The aqueous dispersion of claim 12 wherein said poloxyalkylene ester emulsifying agent is present in the proportion of 60 percent by weight wherein said oxyethylene content is 60 percent by weight of the total weight of said product and wherein said other anionic surfactant is calcium dodecylbenzene sulphonate, present in the amount of 9 percent by weight, and the balance of said emulsifying agent is a nonionic defoaming agent, all weights being based upon the total weight of the emulsifying agent.

14. The aqueous dispersion of claim 11 wherein said emulsifying agent contains a polyoxyalkylene maleic acid half-ester of a 1,4-butanediol-initiated reaction product of 1,2-butylene oxide and ethylene oxide reaction product and wherein the oxyethylene content thereof is sufficient to provide a molecular weight of 40 percent by weight of the total weight of the product, wherein the polyoxyalkylene maleic acid half-ester surfactant is present in the amount of 60 percent by weight of the mixture of surfactants and said other anionic surfactant is calcium dodecylbenezene sulphonate, present in the amount of 9 percent by weight of said mixture and the balance of said emulsifying agent is a nonionic defoaming agent.

* * * * *